(12) United States Patent
Brosha et al.

(10) Patent No.: US 10,490,833 B1
(45) Date of Patent: Nov. 26, 2019

(54) HYDROGEN FUEL QUALITY ANALYZER WITH SELF-HUMIDIFYING ELECTROCHEMICAL CELL AND METHODS OF TESTING FUEL QUALITY

(71) Applicant: LOS ALAMOS NATIONAL SECURITY, LLC, Los Alamos, NM (US)

(72) Inventors: Eric L. Brosha, Los Alamos, NM (US); Tommy Rockward, Los Alamos, NM (US); Christopher J. Romero, Los Alamos, NM (US); Mahlon S. Wilson, Los Alamos, NM (US); Cortney R. Kreller, Los Alamos, NM (US); Rangachary Mukundan, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 112 days.

(21) Appl. No.: 15/805,826

(22) Filed: Nov. 7, 2017

Related U.S. Application Data

(60) Provisional application No. 62/418,597, filed on Nov. 7, 2016.

(51) Int. Cl.
*G01N 27/407* (2006.01)
*G01N 27/403* (2006.01)
(Continued)

(52) U.S. Cl.
CPC ...... *H01M 8/04447* (2013.01); *G01N 27/403* (2013.01); *G01N 27/4075* (2013.01); *G01N 27/49* (2013.01); *H01M 2250/20* (2013.01)

(58) Field of Classification Search
CPC .... G01N 27/49; G01N 27/407; G01N 27/403; G01N 27/4075; H01M 8/00; H01M 8/04119; H01M 8/04291; H01M 8/04492
(Continued)

(56) References Cited

U.S. PATENT DOCUMENTS

| | | | |
|---|---|---|---|
| 5,635,039 A | * | 6/1997 | Cisar ...................... B01D 53/22 |
| | | | 204/252 |
| 6,001,449 A | | 12/1999 | Grot et al. |
| 6,207,312 B1 | * | 3/2001 | Wynne .................. H01M 8/023 |
| | | | 429/480 |

OTHER PUBLICATIONS

Kirby et al., "Detection of low level carbon monoxide in hydrogen-rich gas streams," Sensors and Actuators B, 95:224.231, 2003.
(Continued)

*Primary Examiner* — Luan V Van
*Assistant Examiner* — Caitlyn Mingyun Sun
(74) *Attorney, Agent, or Firm* — Lewis Roca Rothgerber Christie LLP

(57) ABSTRACT

A fuel quality analyzer for detecting contaminants in a fuel supply includes an anode flow field plate defining a first fuel flow field channel and a fuel inlet port, a cathode flow field plate defining a second fuel flow field channel and a fuel outlet port, a polymer electrolyte membrane between the anode and cathode flow field plates, a first electrode between the anode flow field plate and the polymer electrolyte membrane, and a second electrode between the cathode flow field plate and the polymer electrolyte membrane. The second electrode has a higher platinum loading than the first electrode. A reservoir volume is defined by the anode and cathode flow field plates. At least a portion of the polymer electrolyte membrane extends into the reservoir volume. The reservoir volume is configured to retain water to humidify the polymer electrolyte membrane.

20 Claims, 11 Drawing Sheets

(51) Int. Cl.
*H01M 8/0444* (2016.01)
*G01N 27/49* (2006.01)

(58) Field of Classification Search
USPC .......................................................... 204/409
See application file for complete search history.

(56) References Cited

OTHER PUBLICATIONS

Mukundan et al., "A low temperature sensor for the detection of carbon monoxide in hydrogen," Solid State Ionics, 175:497-501, 2004.
Noda et al., "PEFC-type impurity sensors for hydrogen fuels," International Journal of Hydrogen Energy, 37:16256-16263, 2012.
Rockward et al., "VIII.4 Hydrogen Fuel Quality," FY 2015 Annual Progress Report, DOE Hydrogen and Fuel Cells Program, 2015, 5 pages.
Rockward et al., "VIII.5 Hydrogen Fuel Quality," FY 2014 Annual Progress Report, DOE Hydrogen and Fuel Cells Program, 2014, 6 pages.

* cited by examiner

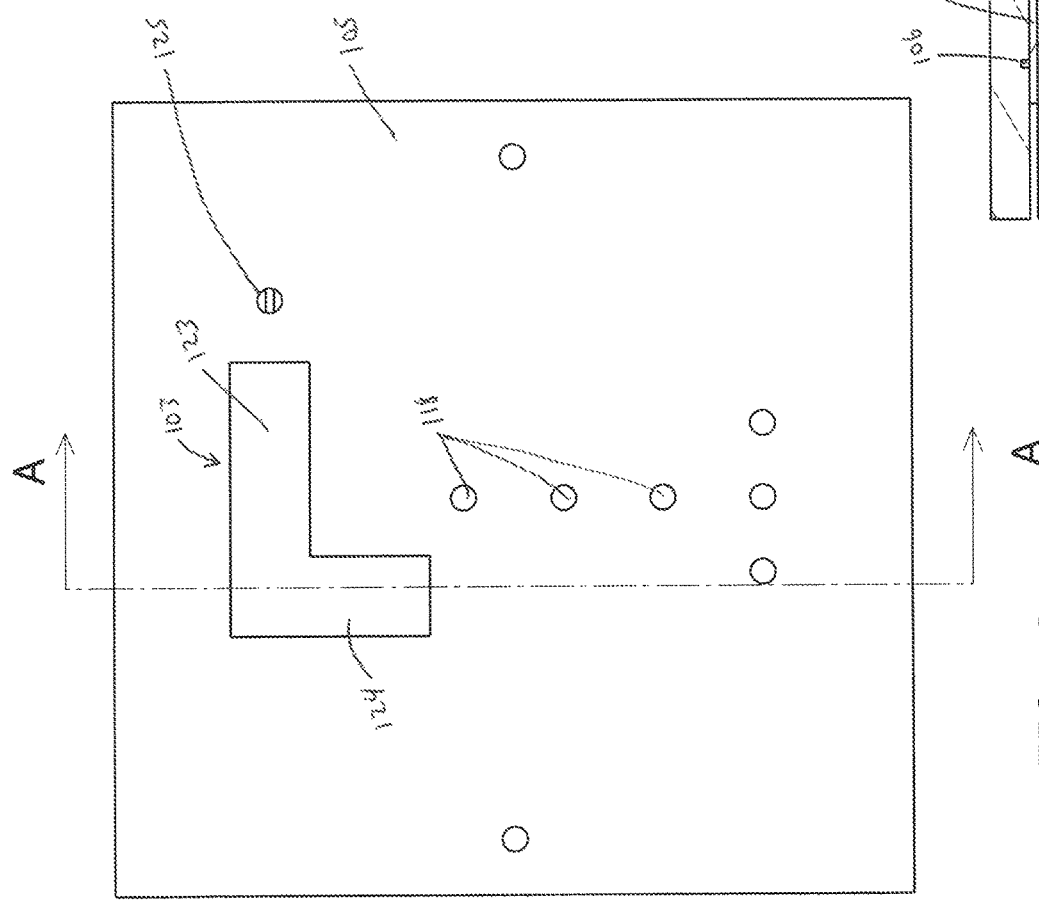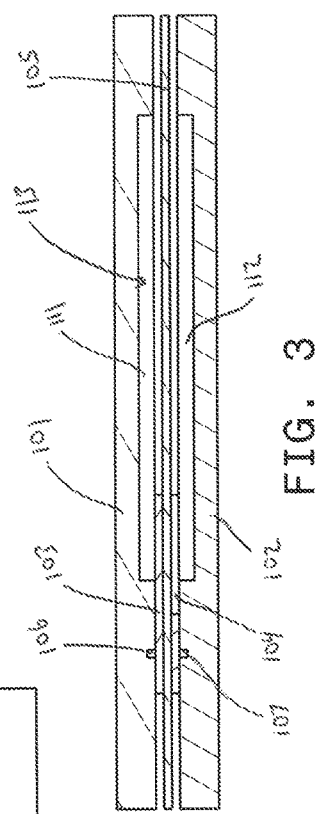

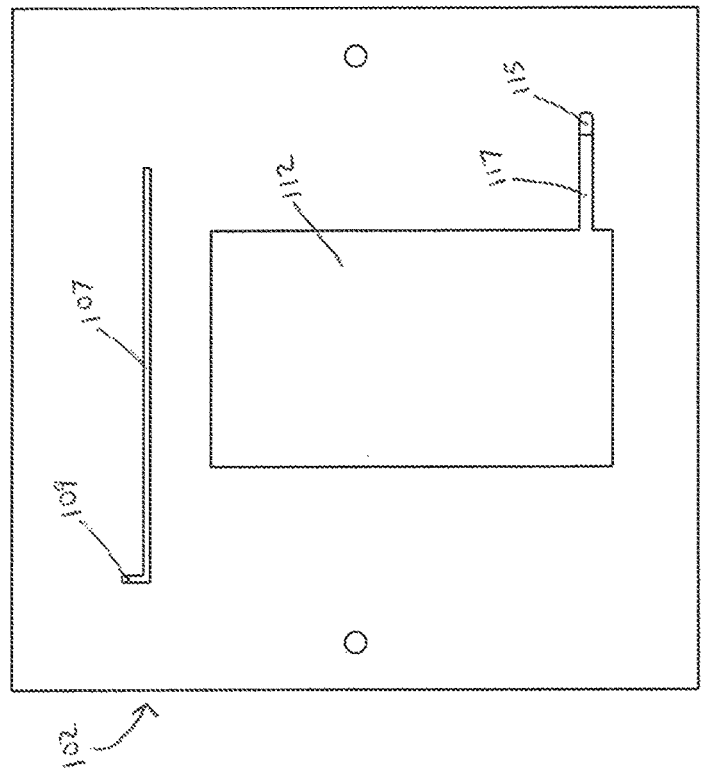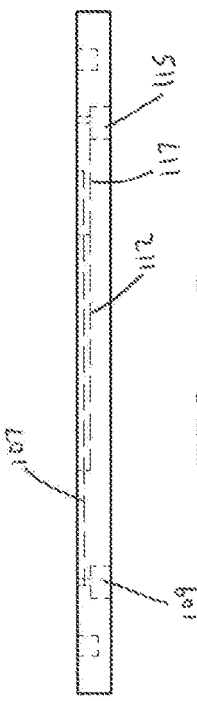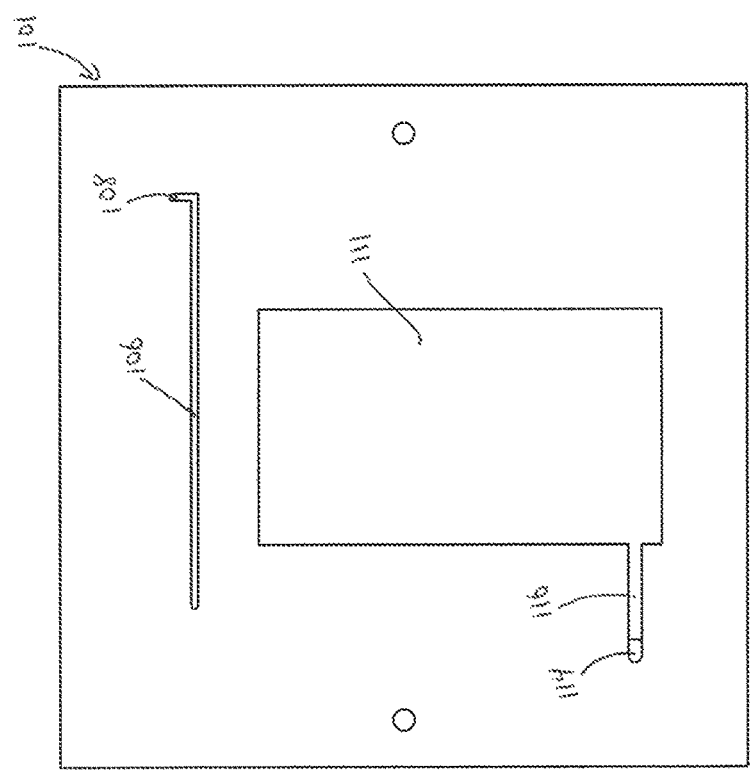
FIG. 4A
FIG. 4B
FIG. 5A
FIG. 5B

HYDROGEN FUEL QUALITY ANALYZER WITH SELF-HUMIDIFYING ELECTROCHEMICAL CELL AND METHODS OF TESTING FUEL QUALITY

CROSS-REFERENCE TO RELATED APPLICATION

This application claims priority to and the benefit of U.S. Provisional Application No. 62/418,597, filed Nov. 7, 2016, the entire contents of which are incorporated herein by reference.

STATEMENT REGARDING FEDERALLY SPONSORED RESEARCH OR DEVELOPMENT

The United States government has certain rights in this invention pursuant to Contract No. DE-AC52-06NA25396 between the United States Department of Energy and Los Alamos National Security, LLC for the operation of Los Alamos National Laboratory.

FIELD

The present disclosure relates generally to hydrogen fuel quality analyzers and methods of analyzing fuel quality.

BACKGROUND

Fuel cells (e.g., polymer electrolyte membrane fuel cells) are an alternative to internal combustion engines in a significant number of transportation vehicles. Conventional fuel cells include a pair of opposing flow plates, an anode and a cathode between the flow plates, and a membrane between the anode and the cathode. The anode includes a catalyst configured to split the hydrogen fuel source into hydrogen ions and electrons. The cathode includes a catalyst configured to utilize available electrons to split the oxygen in the oxidizer source into negative oxygen ions. The membrane is permeable to protons such that the hydrogen ions flow through the membrane and react with the oxidizer gas to form water. The membrane does not conduct electrons and therefore the electrons flow from the anode to the cathode to complete a circuit.

The catalyst material on the anode and cathode and the membrane is highly susceptible to poisoning from impurities in the hydrogen fuel source. These impurities may be present in the chemical feedstock and/or be introduced into the hydrogen during storage and/or delivery to the storage facility. Depending on the species of the impurity and/or the concentration of the impurity, the fuel cell may be permanently damaged due to a single exposure to impurities in the hydrogen fuel source.

Since conventional polymer electrolyte fuel cells are highly susceptible to poisoning from contaminants in the hydrogen fuel, it has been suggested that a fuel cell type electrochemical device may be used as an analyzer to detect the presence of contaminants in a fuel source before delivery of the fuel to the fuel cell. However, fuel cells require water to maintain membrane humidification, which improves membrane ion conductivity and increases performance of the fuel cell. In many conventional fuel cells, the hydrogen fuel source and oxidizer are actively humidified with water to maintain membrane humidification. However, water is considered a potential fuel cell fuel contaminant and hydrogen fuel quality standards set a limit on the amount of water that may be present in the hydrogen fuel. Accordingly, actively humidifying the hydrogen fuel source with water precludes the use of conventional fuel cells as a fuel quality analyzer because water itself is a fuel cell contaminant.

Additionally, operators of hydrogen filling stations could periodically test hydrogen quality, but the levels of impurities would require extractive methods using high-precision analyzers (e.g., gas chromatographs, cavity ring down spectrographs, etc.) that would be expensive and require highly-skilled operators. Additionally, a timely test result within minutes is desirable; otherwise, the time delay (e.g., caused by shipping the sample to be tested at a laboratory) could expose many fuel cell vehicles to contamination before the impurities at the hydrogen filling stations are detected.

SUMMARY

The present disclosure is directed to various embodiments of a fuel quality analyzer for detecting contaminants in a fuel supply. In one embodiment, the fuel quality analyzer includes an anode flow field plate defining a first fuel flow field channel and a fuel inlet port in fluid communication with the first fuel flow field channel, a cathode flow field plate defining a second fuel flow field channel and a fuel outlet port in fluid communication with the second fuel flow field channel, a polymer electrolyte membrane between the anode and cathode flow field plates, a first electrode between the anode flow field plate and the polymer electrolyte membrane, and a second electrode between the cathode flow field plate and the polymer electrolyte membrane. The first electrode has a first platinum loading and the second electrode has a second platinum loading higher than the first platinum loading. The fuel quality analyzer also includes a reservoir volume defined by the anode and cathode flow field plates. At least a portion of the polymer electrolyte membrane extends into the reservoir volume. The reservoir volume is configured to retain water to humidify the polymer electrolyte membrane.

The first platinum loading may have an area density less than approximately 0.1 $mg/cm^2$ and the second platinum loading may have an area density of at least approximately 0.2 $mg/cm^2$. The first platinum loading may have an area density from approximately 0.02 $mg/cm^2$ to approximately 0.04 $mg/cm^2$ and the second platinum loading may have an area density of at least approximately 0.2 $mg/cm^2$.

The first electrode may include a first portion outside the reservoir volume and a second portion extending into the reservoir volume. The first portion may be a main body portion aligned with the first fuel flow field channel and the second portion may be a tab portion extending from an end of the main body portion proximate to the fuel inlet port.

The anode flow field plate may define a water inlet port or a water outlet port and the cathode flow field plate defines the other of the water inlet port or the water outlet port.

The polymer electrolyte membrane may define at least one water pass-through opening.

The polymer electrolyte membrane may define at least one fuel pass-through opening. The at least one fuel pass-through opening is in fluid communication with the first and second fuel flow field channels.

The second electrode may include a main body portion aligned with the second fuel flow field channel and a tab portion extending from an end of the main body portion proximate to the at least one fuel pass-through opening. The tab portion extends into the reservoir volume.

The present disclosure is also directed to various methods of detecting contaminants in a fuel supply. In one embodiment, the method includes supplying the fuel supply to an analyzer. The analyzer includes an anode flow field plate defining a first fuel flow field channel, a cathode flow field plate defining a second fuel flow field channel, a polymer electrolyte membrane between the anode and cathode flow field plates, a first electrode between the anode flow field plate and the polymer electrolyte membrane, and a second electrode between the cathode flow field plate and the polymer electrolyte membrane. The first electrode has a first platinum loading and the second electrode having a second platinum loading higher than the first platinum loading. The analyzer also includes a reservoir volume defined by the anode and cathode flow field plates. At least a portion of the polymer electrolyte membrane extends into the reservoir volume. The method also includes humidifying the polymer electrolyte membrane with water retained in the reservoir volume and measuring a current output of the analyzer operated at a constant voltage.

The fuel supply may not be actively humidified.

The method may also include humidifying the polymer electrolyte membrane with the water retained in the reservoir volume.

The method may also include humidifying the first electrode with the water retained in the reservoir volume. The method may also include humidifying the second electrode with the water retained in the reservoir volume.

The method may also include pumping the water into the reservoir volume through a water inlet port defined in one of the anode flow field plate or the cathode flow field plate. The method may also include pumping the water out of the reservoir volume through a water outlet port defined in the other of the anode flow field plate or the cathode flow field plate. The method may also include capping the water inlet port and the water outlet port, and injecting water having an elevated pressure into the reservoir volume.

Contaminants in the fuel supply may be adsorbed on the first electrode, and the contaminants may decrease the current output of the analyzer. The method may include supplying a humidified fuel source substantially free of contaminants to the analyzer to recover an initial current output of the analyzer before the analyzer was exposed to the contaminants. The method may include applying a voltage across the first electrode and the second electrode to recover an initial current output of the analyzer before the analyzer was exposed to the contaminants. The voltage may be at least approximately 0.6V or at least approximately 1.2V (e.g., approximately 1.5V or greater).

The method may include supplying the fuel supply to the first electrode before supplying the fuel supply to the second electrode to protect the second electrode from poisoning by contaminants in the fuel supply.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

FIG. 2 is a top view of the fuel quality analyzer of FIG. 1A;

FIG. 3 is a cross-sectional view of the fuel quality analyzer of FIG. 2 taken along line A-A;

FIGS. 4A-4B are a top view and a side view, respectively, of an anode flow field plate of the fuel quality analyzer of FIGS. 1A-1B;

FIGS. 5A-5B are a top view and a side view, respectively, of a cathode flow field plate of the fuel quality analyzer of FIGS. 1A-1B;

DETAILED DESCRIPTION

Figure 1A:
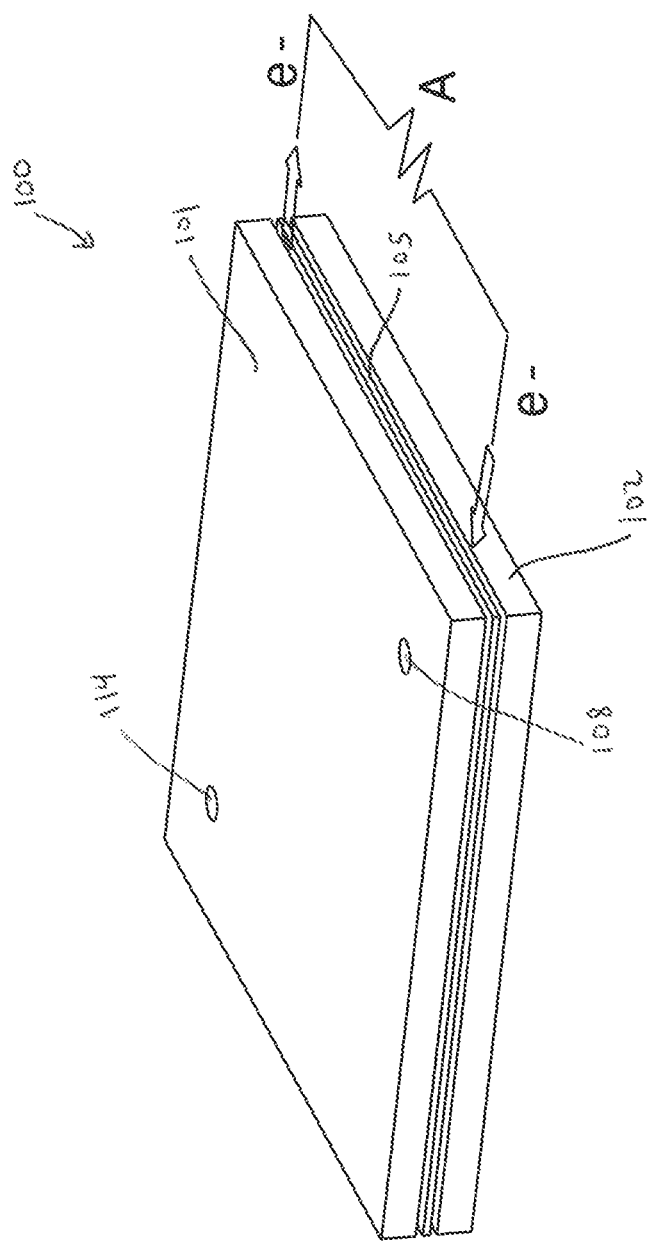
FIG. 1A is a perspective view of a fuel quality analyzer according to one embodiment of the present disclosure.

The present disclosure is directed to various embodiments of an analyzer for detecting the presence of contaminants (e.g., carbon monoxide (CO), hydrogen sulfide, ammonia, and/or hydrocarbons), including contaminants present in a fuel source (e.g., hydrogen gas used in fuel cell vehicles). The analyzers of the present disclosure may be used at a fueling station or in a vehicle incorporating a hydrogen fuel cell system. Additionally, the analyzers of the present disclosure may be used either as in-line analyzers to detect the presence of contaminants in the fuel source before the fuel is sent to a vehicle and/or the analyzers may be used to test a sample of the fuel source that will be disposed of after testing.

The analyzers of the present disclosure are configured to operate in a hydrogen pump mode when a fuel supply (e.g., hydrogen) is fed into the analyzer as a test gas. The hydrogen is oxidized to protons at a first electrode (e.g., a sensing electrode) and the protons recombine leading to hydrogen evolution at a second electrode (e.g., a pseudo reference electrode). The analyzers of the present disclosure are configured to be sensitive to any impurities in the hydrogen that increase its resistance to hydrogen pumping. Additionally, the analyzers of the present disclosure are configured to be more sensitive to contaminants in the fuel supply than conventional polymer electrolyte membrane (PEM) fuel cells (PEMFC).

The presence of contaminants in the fuel supply may be detected by monitoring the output current of the analyzer when operated at a constant voltage. A change or drop in the output current (i.e., the rate at which hydrogen is pumped through the membrane) of the analyzer is indicative of the presence of contaminants in the fuel supply.

Additionally, the analyzers according to various embodiments of the present disclosure are self-humidifying such that the test gas (e.g., hydrogen) may be delivered to the analyzer without humidification or other pre-treatment. Accordingly, $H_2$ having less than 5 parts per million ("PPM") moisture, as regulated by SAE J2719 fuel quality standard, may be delivered to the analyzer without humidification or other pre-treatment. Otherwise, water would be introduced in the humidified fuel source, which is considered a contaminant for PEM fuel cells.

Additionally, the analyzers according to various embodiments of the present disclosure are configured to have a simpler construction and assembly than conventional PEMFCs. The analyzers according to various embodiments of the present disclosure also use less precious metal, such as platinum (Pt), than conventional PEMFCs and thereby have a lower cost than conventional PEMFCs. Additionally, the analyzers according to various embodiments of the present disclosure represent a lower acquisition and operational-cost alternative to conventional high-quality analyzers (e.g., gas chromatographs, spectrometers, etc.).

With reference now to FIGS. 1A, 1B, 2, and 3, a fuel quality analyzer 100 according to one embodiment of the present disclosure includes an anode flow field plate 101, a cathode flow field plate 102 opposite the anode flow field plate 101, a first or working electrode 103 (e.g., a sensing electrode), a second or counter electrode 104 (e.g., a pseudo-reference electrode), and a polymer electrolyte membrane 105 (e.g., NAFION™). The polymer electrolyte membrane 105 is sandwiched between the working electrode 103 and the counter electrode 104, and the polymer electrolyte membrane 105, the working electrode 103, and the counter electrode 104 are all sandwiched between the cathode flow field plate 101 and the anode flow field plate 102. When a constant voltage (i.e., an electric potential) is applied across the electrodes 103, 104 and a fuel (e.g., hydrogen) is pumped through the analyzer 100, the analyzer 100 outputs a current A.

In the embodiment illustrated in FIGS. 1-5, an inner surface of the anode flow field plate 101 facing the membrane 105 defines a fuel flow field channel 106, and an inner surface of the cathode flow field plate 102 facing the membrane 105 defines a corresponding fuel flow field channel 107 (e.g., the anode and the cathode flow field plates 101, 102 each define a single pass flow field 106, 107). Additionally, in the illustrated embodiment, the anode flow field plate 101 defines a fuel inlet port 108 for directing a fuel (e.g., a test fuel sample of hydrogen gas) into the fuel flow field channel 106, and the cathode flow field plate 102 defines a fuel outlet port 109 for directing the fuel out of the fuel quality analyzer 100.

In the illustrated embodiment, the inner surfaces of the anode flow field plate 101 and the cathode flow field plate 102 each define a recess 111, 112, respectively, having a depth less than a thickness of the respective flow field plate 101, 102. In the illustrated embodiment, the recesses 111, 112 are adjacent to the fuel flow field channels 106, 107, respectively. Together, the recesses 111, 112 define a reservoir volume 113 fully enclosed and surrounded by the flow field plates 101, 102. As described in more detail below, the reservoir volume 113 is configured to hold and retain a volume of water to contact and humidify the polymer electrolyte membrane 105, which improves membrane ion conductivity and thereby improves performance of the analyzer 100. Since at least a portion of the polymer electrolyte membrane 105 extends into or through the reservoir volume 113 and is thus exposed to or immersed in the water contained in the reservoir volume 113, the membrane 105 is humidified from the reservoir volume 113. Thus, the fuel (e.g., the test fuel sample of hydrogen) does not need to be humidified before delivery to the analyzer 100. In one or more embodiments, a small amount of water is introduced into the fuel stream, and therefore into the downstream fuel cells, due to evaporative losses inside the analyzer 100 (e.g., a portion of the water in the reservoir volume 113 that is wicked up by the membrane 105 and the electrodes 103, 104 is evaporated into the test fuel stream). However, in one or more embodiments, the amount of water introduced to the test fuel stream (e.g., the test fuel sample of hydrogen) due to evaporative losses is insignificant compared to the volume of the fuel delivered to the analyzer 100 and therefore the introduction of water into the fuel stream due to evaporative losses does not exceed an upper water contamination level set by relevant fuel quality standards. In one or more embodiments, the fuel may be sampled at a sufficiently low gas rate such that the amount of water lost due to evaporation and introduced into the fuel falls within permissible fuel quality standards. In one or more embodiments in which the fuel is sampled at a sufficiently low rate such that the evaporative losses (e.g., the drying of the electrodes 103, 104) and the introduction of water into the test fuel are negligible or otherwise within the limit for permissible fuel quality standards, the test fuel sample may be recombined with the fuel (e.g., the hydrogen) being supplied to the downstream fuel cells. Additionally, in one or more embodiments, the sampling rate of the test fuel stream is a function of the rate at which the fuel (e.g., hydrogen) is being consumed by the downstream fuel cells. Accordingly, in one or more embodiments in which the fuel consumption rate of the fuel cell, and therefore the sampling rate of the test fuel, is sufficiently high such that that the evaporative losses (e.g., the drying of the electrodes 103, 104) and the introduction of water into the test fuel exceeds the limit for permissible fuel quality standards, the test fuel sample may be dumped to air (i.e., the test fuel sample may not be recombined with the fuel being supplied to the downstream fuel cells). In one or more embodiments in which the test fuel sample is dumped to air (e.g., atmosphere), the amount of water introduced into the fuel sample due to evaporative losses within the analyzer 100 is irrelevant because the water is not introduced as a contaminant into the downstream fuel cells.

Additionally, in the illustrated embodiment, the anode flow field plate 101 and the cathode flow field plate 102 each define a water inlet/outlet port 114, 115 (e.g., a through hole) and a groove or channel 116, 117 extending between and connecting the port 114, 115 and the recess 111, 112, respectively. The ports 114, 115 in the anode flow field plate 101 and the cathode flow field plate 102 are configured to direct water into and out from the reservoir volume 113, respectively. The water in the reservoir volume 113 may be continually refreshed (e.g., cycled through the analyzer 100) from a water supply source remote or separate from the analyzer 100. Additionally, in the illustrated embodiment, the polymer electrolyte membrane 105 defines a series of water pass-through openings 118. Water pumped into the reservoir volume 113, for example, from the port 114 in the anode flow field plate 101, is configured to pass through the water pass-through openings 118 in the polymer electrolyte membrane 105 and, for example, out through the port 115 in the cathode flow field plate 102. In one or more embodiments, the water may be pumped into the reservoir volume 113 from the port 115 in the cathode flow field plate 102 and out through the port 114 in the anode flow field plate 101. In the illustrated embodiment, the cross-sectional area of the reservoir volume 113 is smaller than the area of the polymer electrolyte membrane 105 such that only a portion of the polymer electrolyte membrane 105 extends into, and is exposed and immersed in, the reservoir volume 113. A portion of the water pumped into the reservoir volume 113 is absorbed by the portion of the membrane 105 extending into or through the reservoir volume 113, and then the water is wicked along and/or through the membrane 105 to portions of the membrane 105 that do not extend into the reservoir volume 113.

In the illustrated embodiment, the counter electrode 104 is loaded with a relatively higher amount of platinum (Pt) or platinum-ruthenium (Pt-Ru) alloy 119, and the working electrode 103 is loaded with a relatively lower amount of Pt 120. Reducing the Pt loading of the working electrode 103 compared to the counter electrode 104 is configured to increase the sensitivity of the analyzer 100 to contaminants in the fuel (e.g., the test sample of hydrogen fuel). Additionally, in one or more embodiments, the working electrode 103 and/or the counter electrode 104 may be provided without an ionomer such as NAFION™ (e.g., the working electrode 103 and/or the counter electrode 104 may be provided either directly on a gas diffusion layer or on a micro-porous layer). For example, the Pt 119, 120 may be applied, for example, by sputtering, directly on a gas diffusion layer (GDL) material with or without a micro porous layer. In one or more embodiments, the area density of the Pt 120 on the working electrode 103 may be less than approximately 0.1 mg/cm$^2$ and the area density of the Pt or Pt—Ru 119 on the counter electrode 104 benefits from a comparably much higher loading and may be approximately 0.2 mg/cm$^2$ or higher. In one or more embodiments, the area density of the Pt 120 on the working electrode 103 may be from approximately 0.02 mg/cm$^2$ to approximately 0.04 mg/cm$^2$ and the area density of the Pt or Pt—Ru 119 on the counter electrode 104 may be approximately 0.2 mg/cm$^2$ or higher.

Figure 1B:
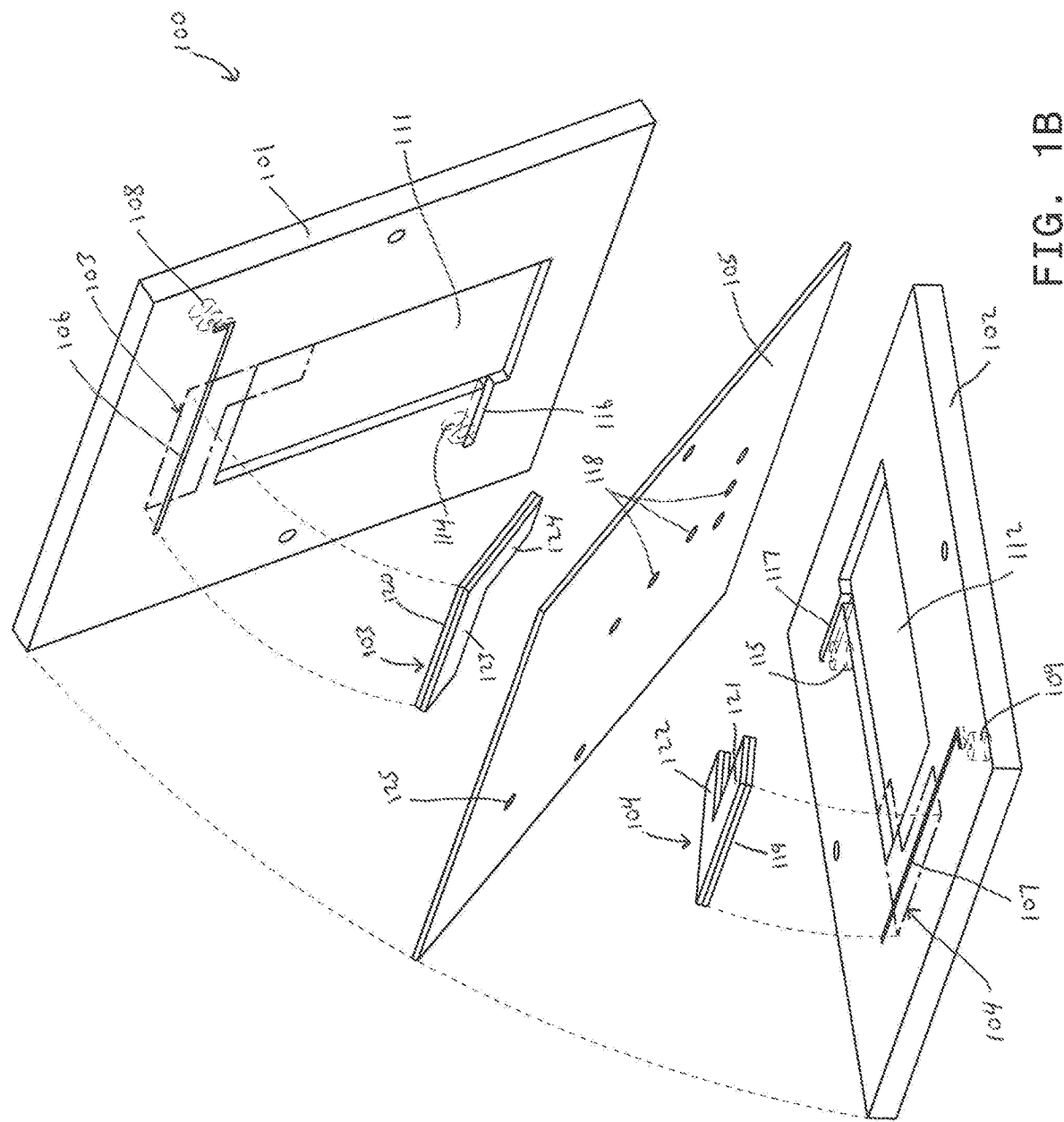
FIG. 1B is an exploded perspective view of the fuel quality analyzer of FIG. 1A.
Figure 7:
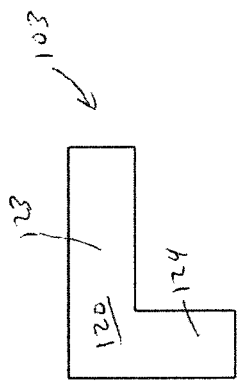
FIG. 7 is a top view of a working electrode of the fuel quality analyzer of FIGS. 1A-1B.
Figure 8:
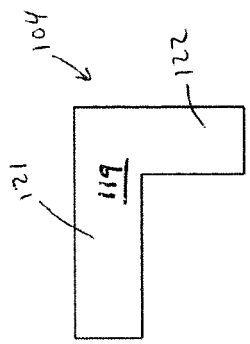
FIG. 8 is a top view of a counter, reference electrode of the fuel quality analyzer of FIGS. 1A-1B.
Figure 6:
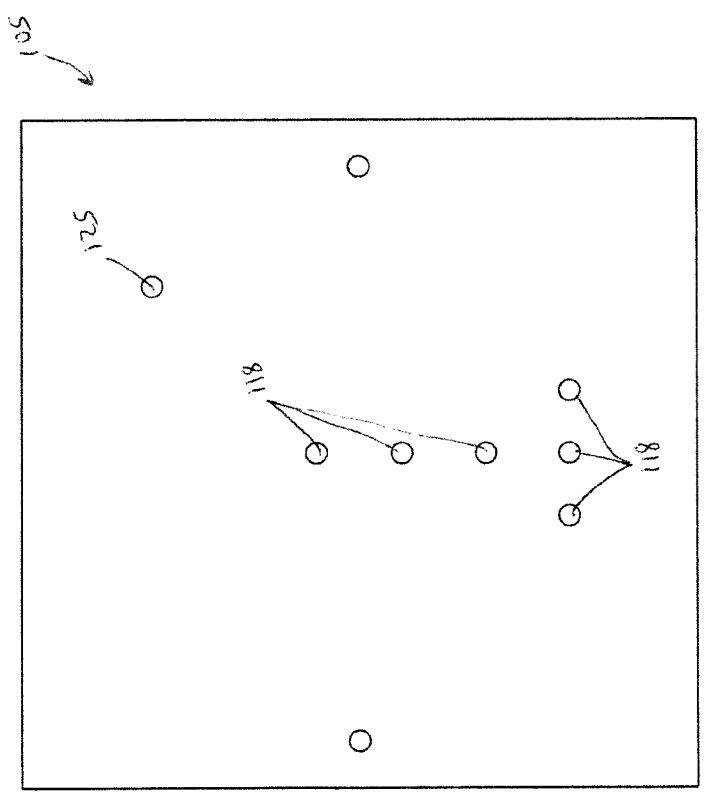
FIG. 6 is a top view of a polymer electrolyte membrane of the fuel quality analyzer of FIGS. 1A-1B.

With reference now to the embodiment illustrated in FIGS. 1B, 7, and 8, the working electrode 103 is L-shaped with a main body portion 123 outside of the reservoir volume 113 (e.g., a main body portion 123 aligned with the fuel flow field channel 106 in the anode flow field plate 101) and a tab portion 124 extending from the main body portion 123 into the reservoir volume 113 (see broken lines in FIG. 1B). In the illustrated embodiment, the tab portion 124 of the working electrode 103 extending into the reservoir volume 113 is located at an end of the working electrode 103 proximate to the fuel inlet port 108 in the anode flow field plate 101 (e.g., the tab portion 124 of the working electrode 103 is at an end of the main body portion 123 proximate to the fuel inlet port 108). Similarly, the counter electrode 104 includes a main body portion 121 (see broken lines in FIG. 1B) outside of the reservoir volume 113 defined by the anode and cathode flow field plates 101, 102 (e.g., a main body portion 121 aligned with the fuel flow field channel 107 in the cathode flow field plate 102) and a tab portion 122 (see broken lines in FIG. 1B) extending from the main body portion 121 into the reservoir volume 113. In the illustrated embodiment, the tab portion 122 of the counter electrode 104 extending into the reservoir volume 113 is located at an end of the counter electrode 104 proximate to a test gas pass-through opening 125 in the membrane 105 (e.g., the tab portion 122 of the counter electrode 104 is at an end of the main body portion 121 proximate to the test gas pass-through opening 125 in the membrane 105), the significance of which is described below.

The portions 122, 124 of the working electrode 103 and the counter electrode 104 extending into the reservoir volume 113 are configured to absorb water in the reservoir volume 113 and wick the water to the portions 121, 123 of the working electrode 103 and the counter electrode 104 outside of the reservoir volume 113. Providing the working electrode 103 and the counter electrode 104 each with a portion 122, 124 that extends into the reservoir volume 113 such that water is transported to the working electrode 103 and the counter electrode 104 enables operating the analyzer 100 at higher flow rates of dry (i.e., non-humidified) gas (e.g., non-humidified hydrogen). The humidification of the electrodes 103, 104 and the membrane 105 provided by the water in the reservoir volume 113 is configured to mitigate an increase in the high frequency resistance (HFR) of the analyzer 100, which would otherwise occur if the electrodes 103, 104 and/or the membrane 105 dried out, and this mitigation against increasing HFR of the analyzer 100 permits higher flow rates of dry gas (e.g., H$_2$) to be flowed through the analyzer 100. For example, in one embodiment, flowing approximately 20 standard cubic centimeters per minute ("SCCM") of dry H$_2$ through the analyzer 100 caused the HFR of the analyzer 100 to increase from an initial value of approximately 0.170 ohm to only approximately 0.910 ohm, which indicates that the electrodes 103, 104 and the membrane 105 of the analyzer 100 remained sufficiently humidified by the water in the reservoir volume 113. In one embodiment, flowing approximately 100 SCCM of dry H$_2$ for over approximately 18 hours caused the HFR of the analyzer 100 to increase from an initial value of approximately 0.170 ohm to approximately 2.136 ohm, which is a stable value indicating that the electrodes 103, 104 and the membrane 105 of the analyzer 100 remained sufficiently humidified. In one or more embodiments, significantly higher flow rates of dry H$_2$ may be flowed through the analyzer 100 without completely drying out the electrodes 103, 104 and the membrane 105. The hydrophobic and hydrophilic properties of the working electrode 103 and the counter electrode 104 (e.g., the TEFLON™ content of the working electrode 103 and the counter electrode 104), as well the size of the portions 122, 124 of the working electrode 103 and the counter electrode 104, may be selected based on the desired amount of water absorbed by the working electrode 103 and the counter electrode 104 and the desired flow rate of the fuel through the analyzer 100. Additionally, in one or more embodiments, the rate of water transport to the electrodes 103, 104 is balanced by the rate of water loss from the electrodes 103, 104 by evaporative losses to the dry test gas being analyzed. In one or more embodiments, for example, the working electrode 103 may be made by sputtering Pt (e.g., using an RF magnetron sputtering process) onto a SGL Sigracet 30AA carbon paper gas diffusion layer (GDL). In one or more embodiments, a Pt—Ru ink containing the catalyst and Nafion™ ionomer is painted on to the counter electrode 104. In one or more embodiments, a Pt—Ru ink containing the catalyst and Nafion™ ionomer is directly painted on to the membrane 105 and the gas diffusion layer (GDL) is pressed on top of it to make the counter electrode 104. In one or more embodiments, the counter electrode 104 is hot pressed using a decal process or painted directly onto the membrane 105 using standard PEMFC processes.

In one or more embodiments, the analyzer 100 also includes one or more gaskets (not shown) between the anode flow field plate 101 and the cathode flow field plate 102. Additionally, in one or more embodiments, the working electrode 103, the membrane 105, and the counter electrode 104 may be compressed between the anode flow field plate 101 and the cathode flow field plate 102 such that the fuel supply may be pressurized and impurities in the pressurized fuel supply may also be analyzed.

In operation, fuel (e.g., a test sample of hydrogen gas) flows through the fuel inlet port 108 in the anode flow field plate 101 and along the fuel flow field channel 106 in the anode flow field plate 101 (i.e., the fuel flows between the anode flow field plate 101 and the working electrode 103 that is humidified by the reservoir volume 113). As the fuel flows along the fuel flow field channel 106 in the anode flow field plate 101, any contaminants in the fuel poison the Pt 120 on the working electrode 103 or get incorporated into the Nafion™ in the membrane 105 or the working electrode 103 (e.g., CO and $H_2S$ contaminants adsorb on the Pt, but $NH_3$ contaminants are incorporated as $NH_4+$ ions into the Nafion™ where they displace H+ and decrease conductivity). When the fuel reaches the end of the fuel flow field channel 106, the fuel flows through the fuel pass-through opening 125 in the polymer electrolyte membrane 105 that is humidified by the water in the reservoir volume 113 and into the fuel flow field channel 107 in the cathode flow field plate 102. The fuel then flows along the flow field channel 107 in the cathode flow field plate 102 (i.e., the fuel flows between the cathode flow field plate 102 and the counter electrode 104 that is humidified by the reservoir volume 113) and out of the fuel outlet port 109 in the cathode flow field plate 102. In this manner, the analyzer 100 exposes the working electrode 103 to any contaminants in the test gas before exposing the counter electrode 104 to any contaminants in the fuel supply, which helps to protect the counter electrode 104 against poisoning and thereby permits the counter electrode 104 to serve as a pseudo-reference electrode. The counter electrode 104, which serves as a pseudo-reference electrode, is also protected against poisoning by virtue of its relatively high catalyst loading. Protecting the counter electrode 104 from poisoning is configured to preserve the full performance of the counter electrode 104 (i.e., the pseudo-reference electrode), while further sensitizing the working electrode 103 to the contaminants.

Additionally, in operation, water is pumped through the port 114 in the anode flow field plate 101 and flows along the groove 116 and into the recess 111 defined in the anode flow field plate 101. The water then flows through the water pass-through openings 118 in the polymer electrolyte membrane 105, into the recess 112 defined in the cathode flow field plate 102, and then along the groove 117 and out through the port 115 defined in the cathode flow field plate 102. In this manner, the water pumped into the reservoir volume 113 is configured to humidify the polymer electrolyte membrane 105, the working electrode 103, the counter electrode 104, and the fuel passing through the analyzer 100. In one or more embodiments, the anode and cathode flow field plates 101, 102 may be provided without the ports 114, 115 or the ports 114, 115 may be capped off or plugged. For example, in one or more embodiments, the ports 114, 115 may be capped off when the analyzer 100 is used to detect the presence of contaminants in test gas streams having relatively high pressures (e.g., a pressure corresponding to a flow rate of approximately 100 SCCM). In an embodiment in which the ports 114, 115 are capped off, the water in the reservoir volume 113 may be periodically replenished after the water has been consumed by the test gas. Additionally, in one or more embodiments in which the ports 114, 115 are capped off and the test gas stream has a higher-than-ambient pressure, the water may be injected into the reservoir volume 113 at an elevated pressure to balance the pressure of the test gas stream flowing through the analyzer 100.

Figure 9A:
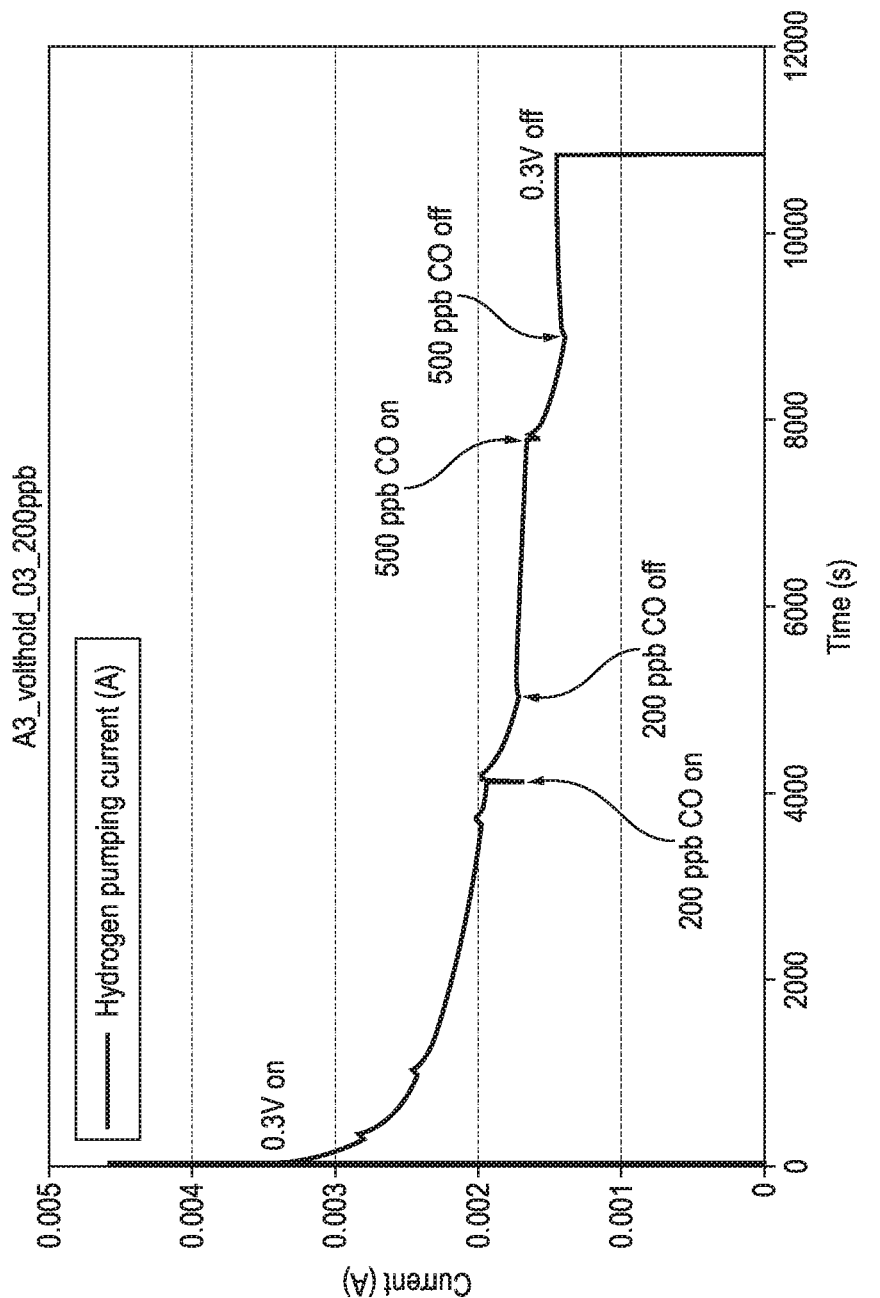
FIGS. 9A-9B are graphs depicting an output current response as a function of exposure to contaminants according to two embodiments of the fuel quality analyzers of the present disclosure.

When a fuel supply free or substantially free from contaminants is pumped into the analyzer 100, the output current A at a fixed supply voltage V of the analyzer 100 is constant or substantially constant. When contaminants are present in the fuel supply, the contaminants (e.g., CO) poison the Pt 120 on the working electrode 103, which causes the output current of the analyzer 100 to drop in proportion to the concentration of the contaminants in the fuel supply. Accordingly, the presence of contaminants in the fuel supply may be detected by monitoring the output current A of the analyzer 100 and monitoring for a drop in the output current A. FIG. 9A illustrates the output current of the analyzer 100 with external humidification of the test gas and without humidification of the membrane 105. As illustrated in FIG. 9A, there is a decrease in the output current A upon exposure of the working electrode 103 to 200 parts-per-billion (ppb) of CO contaminants and, subsequently, a further reduction of the output current A when the working electrode 103 is exposed to a high concentration of CO contaminants (e.g., 500 ppb of CO contaminants).

Figure 9B:
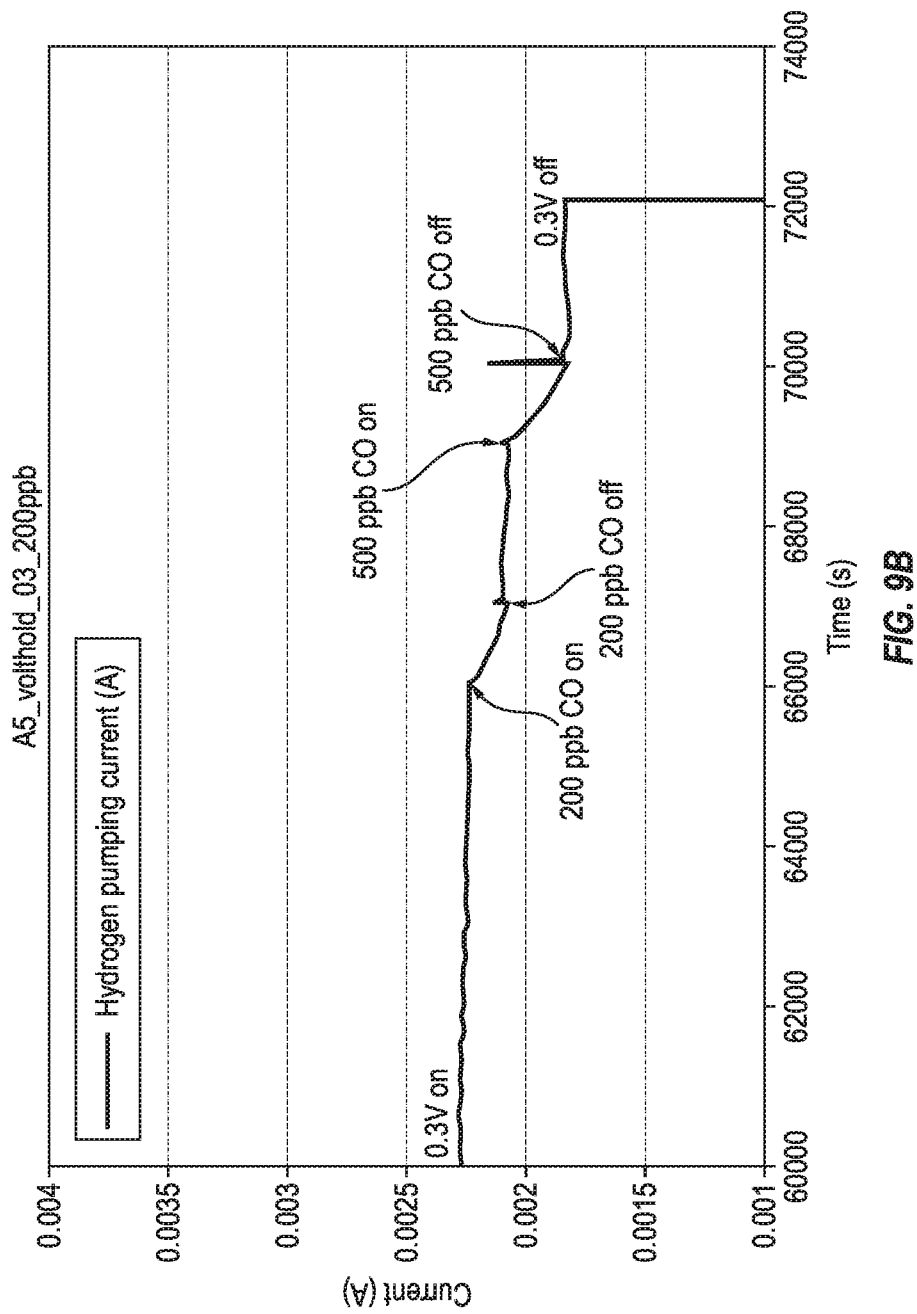

FIG. 9B illustrates the output current A of the analyzer 100 according to one embodiment of the present disclosure when the working electrode 103 is humidified. FIG. 9B illustrates that the performance analyzer 100 when the membrane 105 is humidified according to one or more embodiments of the present disclosure is nearly identical to the performance of the analyzer in FIG. 9A without the need for external humidification of the test gas. FIG. 9B further illustrates the efficiency or efficacy of the analyzer 100 at maintaining membrane 105 humidification when dry gas is flowing through the analyzer 100. As illustrated in FIG. 9B, when approximately 200 ppb of CO contaminants is introduced into a hydrogen fuel supply, the output current A of the analyzer 100 drops. When the source of the CO contaminants is shut off such that the hydrogen fuel supply is free or substantially free from contaminants, the output current of the analyzer 100 returns to being constant or substantially constant. Similarly, as illustrated in FIG. 9B, when 500 ppb of CO contaminants is introduced into the hydrogen fuel supply, the output current of the analyzer 100 drops further, and after the source of contaminants is no longer introduced into the fuel supply (i.e., the source of the contaminants is shutoff), the output current of the analyzer 100 returns to being constant or substantially constant. Accordingly, these drops in the output voltage of the analyzer 100 are indicative of the presence of contaminants in the fuel supply fed into the analyzer 100. The detection of contaminants in the fuel supply is important because, for example, the fuel quality standard SAE J2719 sets the allowable limit of CO contamination in the fuel to 200 ppb.

Figure 10A:
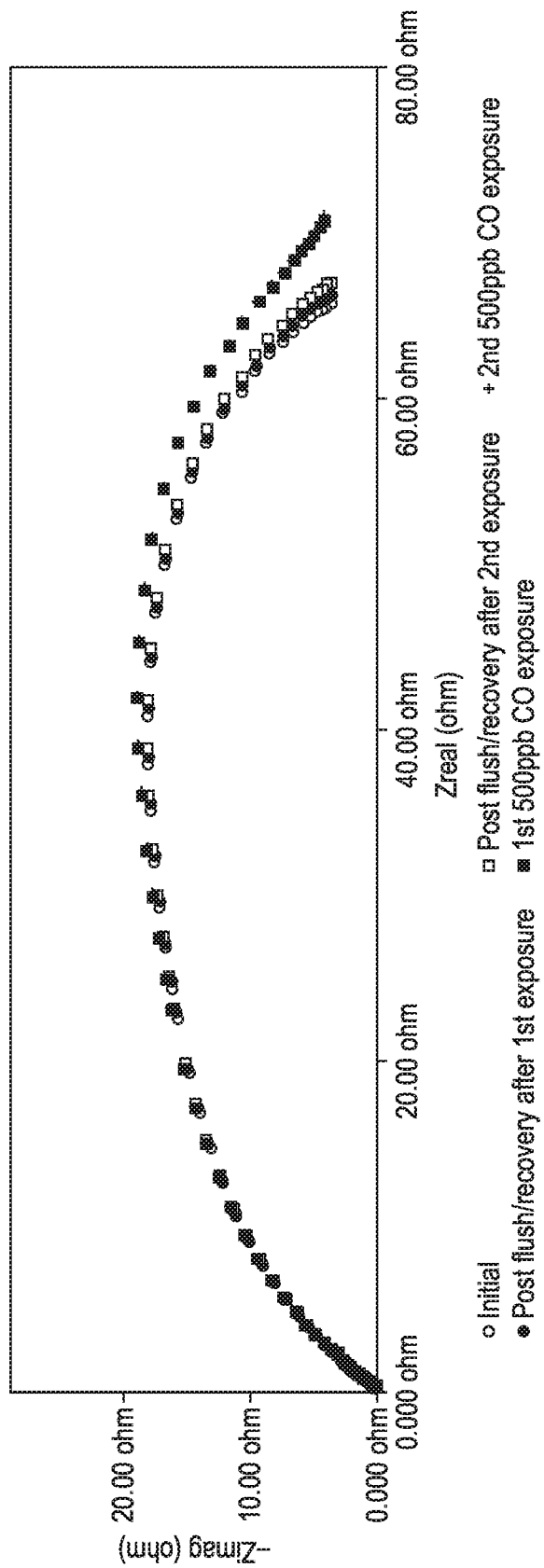
FIGS. 10A-10C are graphs depicting the impedance of the fuel quality analyzer according to one embodiment as a function of contaminant exposure.
Figure 10B:
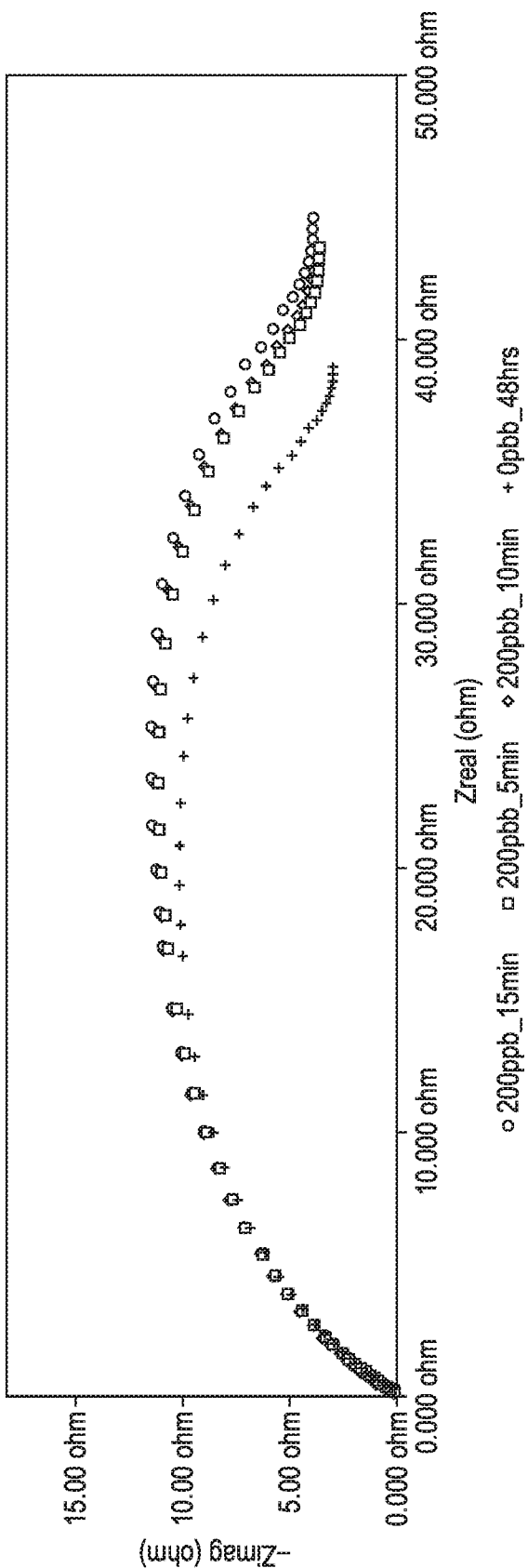
Figure 10C:
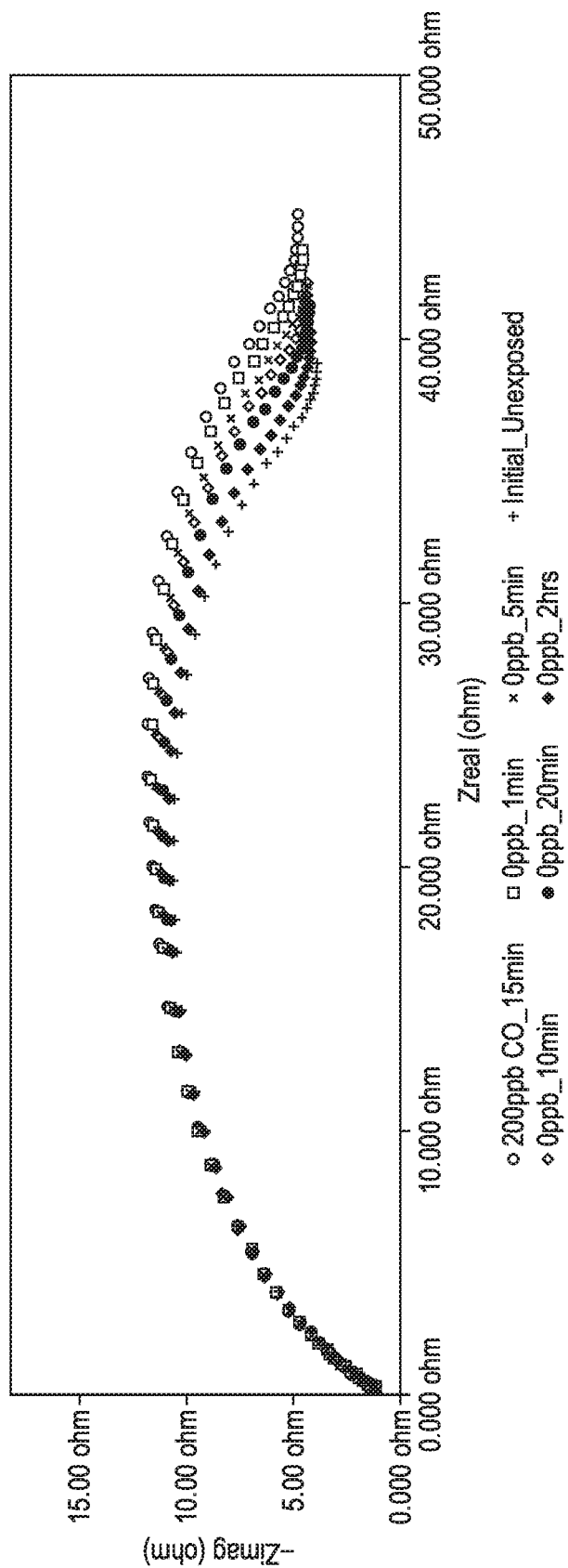

For certain applications, reversing the effects of CO exposure on the analyzer 100 may be desirable if replacement of the electrochemical cell is undesirable (e.g., cost-prohibitive). FIGS. 10A-10C depict, respectively, the impedance at open circuit of the analyzer 100 prior to exposure to contaminants, during exposure to contaminants in a fuel supply, and post-exposure to contaminants for the analyzer 100 using external humidification of the test gas. As shown in FIGS. 10A-10C, the output current response of the analyzer is recoverable (i.e., reversible) following exposure to contaminants in the fuel source if sufficient water is present to aid in the oxidation of the contaminants. For instance, FIG. 10A depicts the output response of the analyzer 100 when subject to 500 ppb of carbon monoxide (CO) in a fuel supply. As illustrated in FIG. 10A, when a fuel supply having approximately 500 ppb of CO contaminants is pumped through the analyzer 100, the resistance (primarily due to the relatively lower Pt-loaded working electrode 103) increases and the current output response of the analyzer 100 decreases. When the contaminants are removed from the fuel supply and the analyzer 100 is pumped with fuel that is free or substantially free of contaminants, the resistance of the relatively lower Pt-loaded working electrode 103 decreases and the current output response of the analyzer 100 recovers to the same or substantially the same current output response of the analyzer 100 prior to exposure to the contaminants in the fuel supply. Similarly, as illustrated in FIG. 10B, when 200 ppb CO contaminants are present in the fuel supply pumped through the analyzer 100, the resistance of the relatively lower Pt-loaded working electrode 103 increases and the current output response of the analyzer 100 decreases. Additionally, as shown in FIG. 10B, the resistance of the relatively lower Pt-loaded working electrode 103 continues to increase over the duration of the exposure to the contaminants (e.g., the resistance of the relatively lower Pt-loaded working electrode 103 was higher after approximately 15 minutes of exposure to contaminants than after approximately 10 minutes of exposure, and the working electrode 103 resistance was higher after approximately 10 minutes of exposure than after only approximately 5 minutes of exposure). However, when the contaminants were removed from the fuel supply and the analyzer 100 was pumped with fuel that is free or substantially free of contaminants for approximately 48 hours, the resistance of the relatively lower Pt-loaded working electrode 103 decreased and the current output response of the analyzer 100 recovered to the same or substantially the same current output response of the analyzer 100 prior to exposure to the contaminants in the fuel supply. Additionally, as illustrated in FIG. 10C, when a fuel supply having approximately 200 ppb of CO contaminants was pumped through the analyzer 100 for approximately 15 minutes, the resistance of the relatively lower Pt-loaded working electrode 103 increased and the current output response of the analyzer 100 decreased. When the CO contaminants were removed from the fuel supply, the resistance of the relatively lower Pt-loaded working electrode 103 decreased and the current output response of the analyzer 100 increased as the exposure time to the pure or substantially pure fuel source increased. FIG. 10C depicts the output response of the analyzer 100 at approximately 1 minute, approximately 5 minutes, approximately 10 minutes, approximately 20 minutes, and approximately 2 hours after the contaminants were removed from the fuel supply. The analyzer 100 according to one or more embodiments of the present disclosure may be "reset" by the injection of water into the test gas until the pre-exposed current value is recovered. Once the electrodes 103, 104 are clean, the injection of additional water is terminated and the analyzer 100 is left to utilize the water reservoir volume 113 for membrane 105 and electrode 103, 104 humidification.

In one or more embodiments, after exposure to contaminants in the fuel, the performance of the analyzer 100 may be reset or recovered by applying an electric potential across the working electrode 103 to desorb (e.g., either through oxidation or reduction of the contaminant species depending on the sign and magnitude of the applied voltage) the contaminants on the working electrode 103. For example, in the case in which the contaminants include CO, an electric potential of at least approximately 0.6V may be applied to the working electrode 103 to desorb the CO contaminants. In the case in which the contaminants include $H_2S$, an electric potential of at least approximately 1.2V may be applied to the working electrode 103 to desorb the $H_2S$ contaminants. In one or more embodiments, an electric potential of at least approximately 1.5V may be applied to the working electrode 103 to desorb the $H_2S$ contaminants. In one or more embodiments, an electric potential of at least 1.5V may be applied for at least approximately 30 seconds to desorb the $H_2S$ contaminants on the working electrode 103. In one or more embodiments, the duration for which the electric potential is applied to the working electrode 103 may vary depending on the magnitude of the electric potential. For instance, in one or more embodiments, the duration may be inversely related to the magnitude of the electric potential such that the duration necessary to desorb the contaminants increases with decreasing electric potential (e.g., an electric potential of approximately 1.2V may need to be applied to the working electrode 103 for a longer duration than an electric potential of 1.5V would need to be applied to the working electrode 103 to adequately desorb the contaminants on the working electrode 103). Applying an electric potential to the working electrode 103 to desorb the contaminants may be performed in addition to, or instead of, running pure or substantially pure fuel through the analyzer 100 to recover the performance of the analyzer 100.

Figure 11:
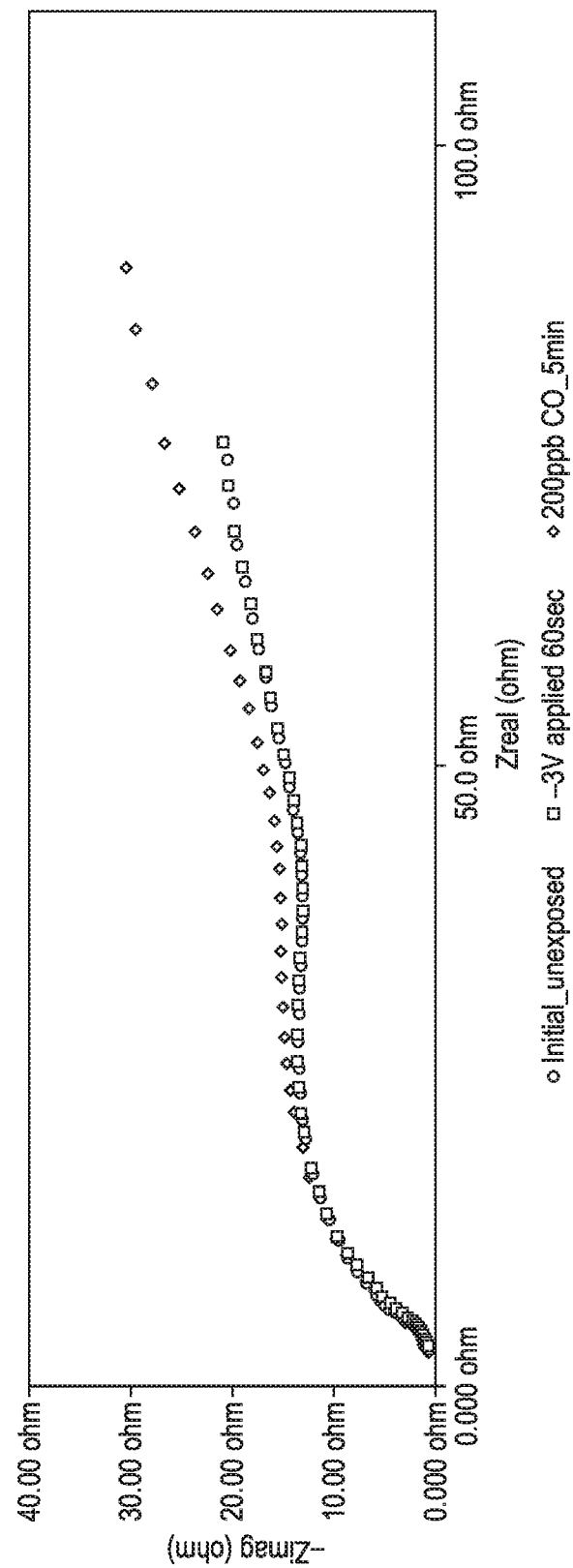
FIG. 11 is a graph depicting the impedance of the fuel quality analyzer according to one embodiment of the present disclosure as a function of contaminant exposure.

FIG. 11 depicts the impedance of the analyzer 100 at a positive voltage bias while the membrane 105 is being humidified solely by the water in the reservoir volume 113 before and after exposure to 200 ppb of CO contaminants in the fuel supply. As illustrated in FIG. 11, the electrode resistance increases as in FIG. 10 and without external humidification of the test gas. However, unlike FIG. 10, the electrode resistance does not return to pre-exposed state over time because of the absence of liquid water in the test gas via external humidification of the gas stream. Instead, FIG. 11 shows that the analyzer 100 returned to the pre-exposed state after a voltage of −0.3V was applied for 60 seconds. The sign of the voltage (i.e., the application of a positive or negative potential) and the magnitude of the applied voltage depend on the amount of water present (e.g., whether self-humidification or water injection-assist is used) and the species of the contaminant. However, both recovery methods have been demonstrated in FIGS. 10 and 11. While this invention has been described in detail with particular references to embodiments thereof, the embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention. Although relative terms such as "inner," "outer," "upper," "lower," and similar terms have been used herein to describe a spatial relationship of one element to another, it is understood that these terms are intended to encompass different orientations of the various elements and components of the invention in addition to the orientation depicted in the figures. Additionally, as used herein, the term "substantially" and similar terms are used as terms of approximation and not as terms of degree, and are intended to account for the inherent deviations in measured or calculated values that would be recognized by those of ordinary skill in the art. Furthermore, as used herein, when a component is referred to as being "on" or "coupled to" another component, it can be directly on or attached to the other component or intervening components may be present therebetween. Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein.

What is claimed is:

1. A fuel quality analyzer for detecting contaminants in a fuel supply, comprising:
    an anode flow field plate defining a first fuel flow field channel and a fuel inlet port in fluid communication with the first fuel flow field channel;
    a cathode flow field plate defining a second fuel flow field channel and a fuel outlet port in fluid communication with the second fuel flow field channel;
    a polymer electrolyte membrane between the anode and cathode flow field plates;
    a first electrode between the anode flow field plate and the polymer electrolyte membrane, and a second electrode between the cathode flow field plate and the polymer electrolyte membrane, the first electrode having a first platinum loading and the second electrode having a second platinum loading higher than the first platinum loading; and
    a reservoir volume defined by the anode and cathode flow field plates,
    wherein at least a portion of the polymer electrolyte membrane extends into the reservoir volume,
    wherein the reservoir volume is configured to retain water to humidify the polymer electrolyte membrane,
    wherein the reservoir volume is separate from each of the first fuel flow field channel and the second fuel flow field channel, and
    wherein at least one of the first electrode or the second electrode comprises a first portion outside the reservoir volume and aligned with the first fuel flow field channel or the second fuel flow field channel, and a second portion extending into the reservoir volume.

2. The fuel quality analyzer of claim 1, wherein the first platinum loading has an area density less than approximately 0.1 mg/cm$^2$ and the second platinum loading has an area density of at least approximately 0.2 mg/cm$^2$.

3. The fuel quality analyzer of claim 1, wherein the first electrode comprises a first portion outside the reservoir volume and a second portion extending into the reservoir volume.

4. The fuel quality analyzer of claim 1, wherein the anode flow field plate defines one of a water inlet port or a water outlet port and the cathode flow field plate defines the other of the water inlet port or the water outlet port.

5. The fuel quality analyzer of claim 1, wherein the polymer electrolyte membrane defines at least one water pass-through opening.

6. The fuel quality analyzer of claim 1, wherein the polymer electrolyte membrane defines at least one fuel pass-through opening, the at least one fuel pass-through opening being in fluid communication with the first and second fuel flow field channels.

7. A fuel quality analyzer for detecting contaminants in a fuel supply, comprising:
    an anode flow field plate defining a first fuel flow field channel and a fuel inlet port in fluid communication with the first fuel flow field channel;
    a cathode flow field plate defining a second fuel flow field channel and a fuel outlet port in fluid communication with the second fuel flow field channel;
    a polymer electrolyte membrane between the anode and cathode flow field plates;
    a first electrode between the anode flow field plate and the polymer electrolyte membrane, and a second electrode between the cathode flow field plate and the polymer electrolyte membrane, the first electrode having a first platinum loading and the second electrode having a second platinum loading higher than the first platinum loading; and
    a reservoir volume defined by the anode and cathode flow field plates,
    wherein at least a portion of the polymer electrolyte membrane extends into the reservoir volume,
    wherein the reservoir volume is configured to retain water to humidify the polymer electrolyte membrane,
    wherein the first electrode comprises a first portion outside the reservoir volume and a second portion extending into the reservoir volume, and
    wherein the first portion is a main body portion aligned with the first fuel flow field channel and the second portion is a tab portion extending from an end of the main body portion proximate to the fuel inlet port.

8. A fuel quality analyzer for detecting contaminants in a fuel supply, comprising:
    an anode flow field plate defining a first fuel flow field channel and a fuel inlet port in fluid communication with the first fuel flow field channel;
    a cathode flow field plate defining a second fuel flow field channel and a fuel outlet port in fluid communication with the second fuel flow field channel;
    a polymer electrolyte membrane between the anode and cathode flow field plates;
    a first electrode between the anode flow field plate and the polymer electrolyte membrane, and a second electrode between the cathode flow field plate and the polymer electrolyte membrane, the first electrode having a first platinum loading and the second electrode having a second platinum loading higher than the first platinum loading; and
    a reservoir volume defined by the anode and cathode flow field plates,
    wherein at least a portion of the polymer electrolyte membrane extends into the reservoir volume,
    wherein the reservoir volume is configured to retain water to humidify the polymer electrolyte membrane,
    wherein the polymer electrolyte membrane defines at least one fuel pass-through opening, the at least one fuel pass-through opening being in fluid communication with the first and second fuel flow field channels,
    wherein the second electrode comprises a main body portion aligned with the second fuel flow field channel and a tab portion extending from an end of the main body portion proximate to the at least one fuel pass-through opening, and
    wherein the tab portion extends into the reservoir volume.

9. A method of detecting contaminants in a fuel supply, the method comprising:
    supplying the fuel supply to an analyzer, the analyzer comprising:
        an anode flow field plate defining a first fuel flow field channel;
        a cathode flow field plate defining a second fuel flow field channel;
        a polymer electrolyte membrane between the anode and cathode flow field plates;
        a first electrode between the anode flow field plate and the polymer electrolyte membrane, and a second electrode between the cathode flow field plate and the polymer electrolyte membrane, the first electrode having a first platinum loading and the second electrode having a second platinum loading higher than the first platinum loading; and a reservoir volume defined by the anode and cathode flow field plates, wherein at least a portion of the polymer electrolyte membrane extends into the reservoir volume, wherein the reservoir volume is separate from each of the first fuel flow field channel and the second fuel flow field channel, and wherein at least one of the first electrode or the second electrode comprises a first portion outside the reservoir volume and aligned with the first fuel flow field channel or the second fuel flow field channel, and a second portion extending into the reservoir volume;

humidifying the polymer electrolyte membrane with water retained in the reservoir volume; and measuring a current output of the analyzer operated at a constant voltage.

10. The method of claim 9, wherein the fuel supply is not actively humidified.

11. The method of claim 9, further comprising humidifying the polymer electrolyte membrane with the water retained in the reservoir volume.

12. The method of claim 9, further comprising humidifying the first electrode with the water retained in the reservoir volume.

13. The method of claim 9, further comprising humidifying the second electrode with the water retained in the reservoir volume.

14. The method of claim 9, further comprising pumping the water into the reservoir volume through a water inlet port defined in one of the anode flow field plate or the cathode flow field plate.

15. The method of claim 14, further comprising pumping the water out of the reservoir volume through a water outlet port defined in the other of the anode flow field plate or the cathode flow field plate.

16. The method of claim 15, further comprising capping the water inlet port and the water outlet port, and injecting water having an elevated pressure into the reservoir volume.

17. The method of claim 9, wherein contaminants in the fuel supply are adsorbed on the first electrode, the contaminants decreasing the current output of the analyzer, and wherein the method further comprises supplying a humidified fuel source substantially free of contaminants to the analyzer to recover an initial current output of the analyzer before the analyzer was exposed to the contaminants.

18. The method of claim 9, wherein contaminants in the fuel supply are adsorbed on the first electrode, the contaminants decreasing the current output of the analyzer, and wherein the method further comprises applying a voltage across the first electrode and the second electrode to recover an initial current output of the analyzer before the analyzer was exposed to the contaminants.

19. The method of claim 18, wherein the voltage is at least approximately 0.6V or at least approximately 1.5V.

20. The method of claim 9, wherein the supplying the fuel supply to the analyzer comprises supplying the fuel supply to the first electrode before supplying the fuel supply to the second electrode to protect the second electrode from poisoning by contaminants in the fuel supply.

\* \* \* \* \*